US006338969B1

(12) United States Patent
Shareef et al.

(10) Patent No.: US 6,338,969 B1
(45) Date of Patent: Jan. 15, 2002

(54) ASSAY TEST SYSTEM FOR REGULATING TEMPERATURE

(75) Inventors: Nazeer H. Shareef, Mishawaka; Jack L. Zuidema, Elkhart, both of IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/440,075

(22) Filed: Nov. 15, 1999

(51) Int. Cl.⁷ ............... G01N 33/543; G01N 21/77; G01N 21/00; G01N 31/22
(52) U.S. Cl. ............... 436/518; 422/58; 436/169
(58) Field of Search ............... 422/58, 64; 435/4; 436/518, 169

(56) References Cited

U.S. PATENT DOCUMENTS

| 4,632,901 A | * | 12/1986 | Valkirs et al. ............... 435/5 |
| 4,847,470 A | | 7/1989 | Bakke ............... 219/299 |
| 5,221,448 A | | 6/1993 | Weinberger et al. ............... 204/26 |
| 5,232,667 A | | 8/1993 | Hieb et al. ............... 422/82.04 |
| 5,827,478 A | * | 10/1998 | Carey et al. ............... 422/58 |
| 6,027,943 A | * | 2/2000 | Kang et al. ............... 436/518 |
| 6,132,682 A | * | 10/2000 | Christner et al. ............... 422/58 |
| 6,197,494 B1 | * | 3/2001 | Oberhardt ............... 435/4 |

* cited by examiner

*Primary Examiner*—Jill Warden
*Assistant Examiner*—Samuel P. Siefke
(74) *Attorney, Agent, or Firm*—Jerome L. Jeffers

(57) ABSTRACT

Disclosed is a dry assay device for carrying out immunochromatographic assays. The device involves an assay strip contained in the interior of a plastic cassette along with a thermally conductive material in thermal communication with the assay strip to more rapidly bring the strip's temperature to that of the ambient.

10 Claims, 1 Drawing Sheet

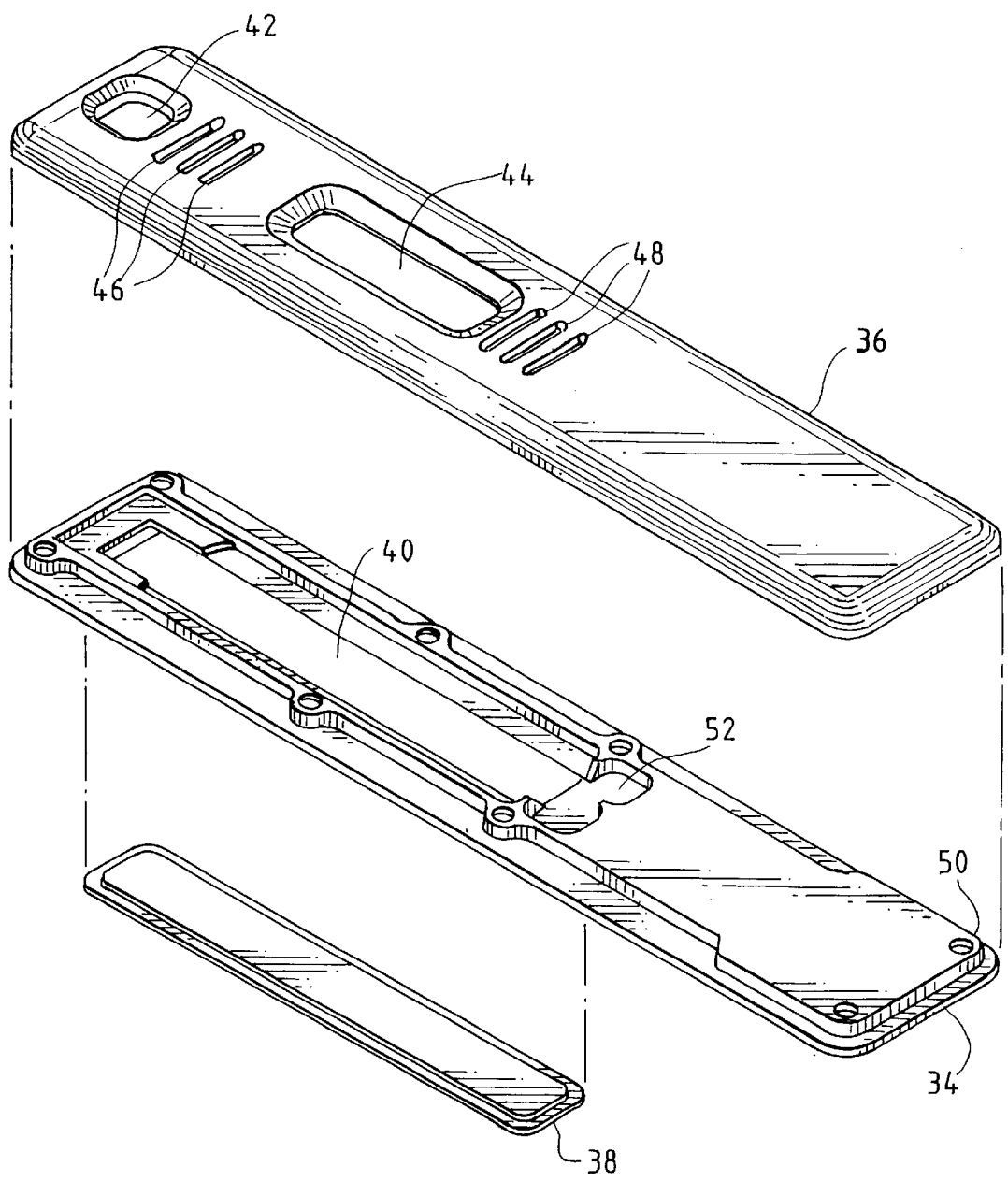

ASSAY TEST SYSTEM FOR REGULATING TEMPERATURE

BACKGROUND OF THE INVENTION

Immunochromatographic strip formats have become increasingly popular for qualitative and semi-quantitative assays which use visual detection schemes. This type of assay involves the application of a liquid test sample suspected of containing an analyte to be detected to an application zone of an immunochromatographic test strip. The strip is comprised of a matrix of absorbant material through which the test fluid and reagents for detecting the analyte can flow by capillarity from the strip's application zone to a capture zone where a detectable signal, or the absence thereof, reveals the presence of the analyte. Typically, the strip will include means for immunospecifically binding the analyte to be detected with its specific binding partner which bears the detectable label. In one such scheme, the strip contains an enzyme labeled, mobile binding partner for the analyte which is located in a zone downstream from the sample application zone. If analyte is present in the test sample, it will combine with its labeled binding partner to form a complex which will flow along the strip to a detection zone which contains a substrate for the enzyme label which is capable of providing a colored response in the presence of the enzyme. The strip may contain a zone in which the analyte is immobilized, so that labeled binding partner which does not combine with analyte, due to the absence of analyte in the sample, will be captured and thereby inhibited from reaching the detection zone. There have been various modifications of this technique, all of which involve some competitive specific binding system in which the presence or absence of analyte in the test sample is determined by the detection or lack thereof of labeled binding partner in the detection zone.

An alternative to the above described immunometric assay which detects the free labeled binding partner is the so called sandwich format in which the capture zone contains immobilized antibodies against an epitope of the analyte which is different from the epitope to which the labeled antibody is specific. In this format, there is formed a sandwich of the analyte between the immobilized and labeled specific binding partners and it is therefore an immunometric assay which detects the bound, labeled specific binding partner.

Not all of the schemes for immunochromatography rely on an enzyme labeled binding partner/enzyme substrate for providing the signal for detection of the analyte. In U.S. Pat. No. 4,806,311 there is disclosed a multizone test device for the specific binding assay determination of an analyte and an immobilized binding partner therefore together with a capture zone for receiving labeled reagent which migrates thereto from the reagent zone. The capture zone contains an immobilized form of a binding substance for the labeled reagent. The labeled reagent bears a chemical group having a detectable physical property, so that it does not require a chemical reaction with another substance in order to be detected. Exemplary of such groups are species of fluorescers, phosphorescent molecules, radioisotopes and electroactive moieties.

U.S. Pat. No. 4,703,017 describes the use of visible particulate labels for the receptor. Various particulate labels such as gold sol particles and visible dye containing liposomes are mentioned. In WO-96/34271 there is disclosed a device for determining a target analyte and creatinine in a fluid test sample which device has an assay strip for the detection of creatinine and a second assay strip for the detection of the target analyte. The creatinine concentration can be determined colorimetrically or by the specific capture of labeled creatinine binding partners. The concentration of the target analyte is corrected based on the sample's creatinine concentration which correction can either be done manually or by means of a properly programmed reflectance analyzer.

Immunochromatographic strip formats provide a viable system for the determination of various analytes (whether they be antigens or antibodies) but suffer from the limitation that they yield results which are at best semi-quantitative when, for some analytes, more precise, quantitative results are required. One variable which needs to be controlled in analyses using immunochromatographic strips is temperature control. Temperature is an important variable because all immunochemical reactions are characterized by two temperature dependent opposite reactions at the same time. These are the formation of an immune complex from an antigen and its antibody and the appearance of free antigen and antibody by dissociation of the immuno complex. Increasing the temperature increases the rate of reaction, and because immunochromatic strip formats are usually measured under non-equilibrium conditions due to the short assay times involved, temperature control, both within and between laboratories, is critical for insuring consistent reaction rates thereby providing more reproducible assay quantitation. Currently, temperature is not controlled. Typically immunochromatographic strips are run at ambient temperature which can range from 20–30° Centigrade. Using the rule of thumb that reaction rates double for every 10 degree centigrade increase in temperature, it is apparent that controlling temperature allows for control of the immunochemical reaction thereby leading to more reproducible results.

Various means for controlling temperature in conjunction with analytical devices are available. In U.S. Pat. No. 5,221,448 there is disclosed an electrophoresis instrument including a capillary tube in an air-cooled cartridge. The cartridge also supports a spherical lens which is part of the optical detection apparatus. The cartridge rests in a manifold which includes the sample and buffer reservoirs. Measuring the electrical resistance of the capillary tube during the electrophoresis process controls the temperature of the capillary tube and cooling or heating of the cartridge is accomplished by circulating temperature controlled air over the tube.

In U.S. Pat. No. 5,232,667 there is disclosed a temperature control system for a disposable cartridge including a sample chamber in which a medical diagnostic device or other electrochemical analytical device is enclosed. The disposable cartridge may include its own heating element on a sensor chip and plugs into a terminal which contains electrical input/output connections. The outer surface of the chip is exposed and a remote temperature sensor, which senses the temperature of the outer surface of the chip of the measuring cell and generates a control signal, is used with conventional temperature control circuitry as the basis for thermostatic control of the cell temperature.

U.S. Pat. No. 4,847,470 discloses an apparatus for warming blood from storage to physiologic temperatures at transfusion rates up to 160 milliliters per minute and includes a flat metal cartridge formed by a pair of thin, generally rectangular, planar members spaced slightly apart in parallelism and sealed at their peripheral edges to define one or more thin, constant width and uniform in thickness ribbon like conduits through which blood flows from an inlet port to an outlet port at opposite ends of the cartridge.

SUMMARY OF THE INVENTION

The present invention is a dry assay device for determining the concentration of at least one analyte in a fluid test sample. The device comprises a strip of absorbant material through which the fluid test sample can flow which strip has a region containing specific binding partners for the analyte which binding partners are marked with a detectable label and a separate detection region for the labeled binding partners. The invention comprises an improvement which involves placing the strip in a hollow casing constructed of a fluid test sample impervious solid material having a top and a bottom which when mated provide a hollow chamber which chamber is in fluid communication with the exterior of the casing and which casing provides an aperture through which the detection region can be observed from outside the casing. The casing contains a thermally conductive material in thermal communication with the strip of absorbant material.

Also included within the scope of the present invention is the method of carrying out an immunochromatographic assay using the device described above.

BRIEF DESCRIPTION OF THE DRAWING

The drawing depicts the top and bottom of the casing and a strip of thermally conductive material which fits into the casing, represents the device of the present invention.

DETAILED DESCRIPTION OF THE INVENTION

Referring to FIG. 1, the casing bottom 34 is designed to mate with the casing top 36 after inserting the thermally conductive material 38 into well 40 of the casing bottom. After inserting the thermally conductive material into the casing bottom's well 40 the strip (not shown) is laid over it and the top and bottom of the cassette are mated to form a unitary device. A strip suitable for use in the present invention is more fully described in co-pending application Ser. No. 259,353 which is jointly assigned and incorporated herein by reference. The casing top has an application port 42 through which the liquid test sample is applied and a viewing port 44 through which the detection zone can be viewed. Slits 46 and 48 through the top of the casing are optional and can be used for venting purposes. The top and bottom of the casing are fabricated to form a hollow chamber 40 when mated. Before mating, the bar of thermally conductive material 38 is placed in the well and the strip is placed over and in thermal communication with this bar. Preferably, the strip and bar are in physical contact with each other. The casing is designed so that the application region of the strip (which may be the first region containing the labeled specific binding agent or a separate region of the strip) is aligned with the sample application port 42 and the detection region of the strip is aligned with the viewing port 44 when the top and bottom of the casing are mated. The casing bottom can be equipped with a series of sockets (illustrated by 50) which lock up with pins (not shown) in the top of the casing when the top and bottom of the casing are mated, to hold them snugly together. Depression 52 in the bottom of the strip is optionally present to hold a desiccant.

The strip can be prepared from any matrix material through which the test fluid carrying the analyte, labeled binder-analyte contained therein can flow by capillarity and can be of a material which is capable of supporting non-bibulous lateral flow as described in U.S. Pat. No. 4,943,522 as liquid flow in which all of the dissolved or dispersed components of the liquid are carried through the matrix at substantially equal rates and with relatively unimpaired flow as contrasted to preferential retention of one or more components as would be the case if the matrix material were capable of absorbing or imbibing one or more of the components. An example of such matrix material is the high density or ultra high molecular weight polyethylene sheet material from Porex Technologies. Equally suitable for use as the matrix from which the chromatographic strip can be fabricated are bibulous materials such as paper, nitrocellulose and nylon.

Various immunochromatographic strip formats are suitable for use in the present invention. The strip typically has a first region, i.e. reagent pad, that is made of an absorbant material such as paper or a membrane that has been impregnated with a reagent associated with a particular test to be performed. An adhesive backing can be placed on a pad of the matrix material which is then cut to a strip of the desired length and width. In conventional immunochromatographic devices, the strip is then placed into the well 40 of the casing so that the reagent pad is located under the sample application port 42. Alternatively, the strip can have an application zone which is free of reagent with the reagent region being down stream and in liquid communication therewith. A particularly suitable format is that which is disclosed in U.S. Pat. No. 4,446,232 in which there is described a device for the determination of the presence of antigens as analyte, which device comprises a strip of matrix material having a detection region in which there are provided immobilized analyte and a first region containing enzyme linked antibodies specific to the analyte to be detected. Upon application of the test fluid to the strip, labeled antibodies located in the first region of the strip can flow with the liquid sample to the detection zone containing the immobilized analyte and a substrate for the enzyme label. If there is analyte in the test fluid the labeled antibodies will react with it and be unavailable for reaction with the immobilized analyte. In the absence of analyte, the labeled antibodies will be available to react thereby capturing the enzyme labeled antibodies which react colorimetrically by the interaction of the enzyme label with the substrate therefore. The analyte is typically an antigen, although the format can be designed to detect the presence of antibodies as analyte. An alternative to this format is a sandwich format in which the labeled antibody is specific for one epitope of the analyte and there is immobilized in the detection zone a second antibody which is specific to a second epitope of the analyte so that there is formed in the detection zone an antibody-analyte-labeled antibody sandwich when analyte is present in the fluid test sample. As an alternative to the use of an enzyme label, the antibodies used in the system can be labeled with a visible, particulate label such as a colored latex or a metal sol. Any physically detectable signal generator can be used as the label.

The present invention involves the inclusion of a thermally conductive material in the cassette to assist in maintaining the test strip at the desired level. As previously discussed, control of the temperature at a predetermined level is desirable in assays which involve the use of immunochromatographic strips. However, when the strip is placed in a plastic cassette, a long incubation period is required to bring the strip to ambient temperature because plastic is only marginally thermally conductive. In order to increase the thermal conductivity of the assay device, there is included in the device a thermally conductive material which is in thermal communication with the immunochromatographic strip and is capable of accelerating the warming or cooling of the strip to the ambient temperature.

The thermally conductive material can be any material which is more thermally conductive than the casing for the strip, which casing is typically made of plastic. Typically, plastics such as high impact polystyrene, ABS or styrene can be used as the plastic material. Metals such as copper, gold and silver are preferred as the thermally conductive material. Among the highly thermally conductive metals, aluminum is preferred due to its good thermal conductivity and low cost. Alloys with superior thermal properties and low cost can be effectively used. A preferred embodiment of the present invention is depicted in the drawing wherein the well 40 of cassette bottom 34 is designed to carry a bar of the thermally conductive material 38, e.g. aluminum. Configurations other than the bar depicted in the drawing are possible, since any configuration which serves the purpose of efficient heat transfer thereby satisfying the functional requirements can be used. The only requirement is that it be in thermal communication with the assay strip, so that it can contribute to bring the strip to the desired temperature and maintain it at that temperature during the assay. Typically, a bar of aluminum is used in direct contact with the assay strip. It is preferred to have physical contact between the metal bar and the assay strip for optimal heat transfer. If for some reason the contact is not perfect, the space around the strip will be heated due to convective heat transfer, so that direct physical contact between the strip and the metal bar is not essential. The size of the bar is not critical so long as sufficient area of the metal is available for heat transfer inside the cassette to satisfy the requirement that the assay strip's temperature is controlled. The metal bar is preferably thin, i.e. about 1.2 mm, since the thinner the inserted bar, the quicker the increase in temperature. The area of the metal bar is another factor which influences the heat transfer capability of the device. The larger the area, the more heat transfer to the strip. Accordingly, the area of the metal bar depends on the configuration of the cassette. The area also depends on the length of the strip which needs temperature control.

In operation, the device is used by pipetting the fluid test sample, which is typically urine, through the sample application port 42 onto the first region of the strip or optional sample application pad. Upon flowing through the first zone of the strip the fluid test sample contacts the labeled antibodies which flow along with the fluid test sample towards the detection zone where the labeled antibodies are captured either by interaction with immobilized analyte or interaction between analyte in the fluid test sample, the labeled antibodies specific thereto and antibodies immobilized in the capture zone which are specific to another epitope on the analyte to form a sandwich. Regardless of how the labeled antibodies are captured in the detection zone there will be a detectable response (absence of signal in the first case) which can be read by a properly programmed reflectance spectrometer.

Many clinically significant target analytes are present in urine and are determinable by means of the type immunochromatographic strips contemplated herein. Among these analytes are deoxypyridinoline, human serum albumin and drugs of abuse such as amphetamines, barbiturates and cocaine. While the means for detecting the signal from the developed strip of the device of the present invention will depend on the detectable label attached to the labeled binding partner, the use of a reflectance spectrometer is typical when the label's detectable physical property is the reflectance of light at a predetermined wavelength. In a preferred method of using the device, there is provided a reflectance meter with means for moving the cassette containing the strip or the meter's detector element relative to each other such as by use of a specimen table for the strip which can be moved laterally under the readhead of the detector. As previously discussed, maintenance of careful temperature control increases the accuracy of the assay.

An assay device confirming to the present invention in which the thermally conductive material is aluminum, was prepared providing a plastic, injection molded base with an aluminum bar having an area similar to that of the assay strip molded in place. It is preferable that the metal bar be wider than the strip in those areas of the strip in which immuno reactions take place and hence require careful temperature control. A reagent test strip was placed over the aluminum bar and the top of the cassette was press fitted (pin to socket) to provide an assembly according to the invention which was 3.12 inches long, 0.75 inch wide and 0.16 inch high.

The temperature differential between the aluminum plate temperature and the reagent strip temperature was determined for different ambient conditions of temperature and humidity and the information was stored in a microprocessor. This information, along with the input information about the current temperature and humidity was used to regulate the current through a heating device, using either a peltier or resistive heater, such that a constant, pre-determined temperature was maintained in the strip. The system was tested to determine the time required for the reagent strip to reach 30° Centigrade. In this experiment a plastic cassette without a metal insert was used as control. A thermocouple was mounted on top of the strip and the cassette without the aluminum bar was placed in an environmental control chamber which was maintained at approximately 30° C. It took approximately seven minutes for the strip to reach 30° C. from its initial temperature of about 25° C. resulting in a temperature increase of 5° C. in seven minutes. A similar cassette with the metal insert in the bottom took approximately one minute for the reagent strip's temperature to reach 30° C. from an initial temperature of 18° C.

The results of this experiment demonstrate that using a simple design can provide rapid thermal transfer if a material with good thermal conductivity is placed in the cassette. The cassette can be made to be disposable since the incremental cost of the thermally conductive insert is minimal.

What is claimed is:

1. In a dry assay device for determining the concentration of at least one analyte in a fluid test sample which device comprises a strip of absorbant material through which the test fluid can flow which strip has a first region containing specific binding partners for the analyte which are marked with a detectable label and a separate detection region for the labeled binding partners the improvement which comprises in combination a the strip within a hollow casing constructed of a fluid test sample impervious solid material having a top and a bottom which when mated provide a hollow chamber suitable for holding the strip, which chamber is in fluid communication with the exterior of the casing and which casing provides a pathway through which the detection region can be observed from outside the casing and contains a thermally conductive material in thermal communication with the strip of absorbant material.

2. The assay device of claim 1 wherein the thermally conductive material lies beneath and in physical contact with the strip of absorbant material.

3. The assay device of claim 1 wherein the casing is made of plastic.

4. The assay device of claim 1 wherein the thermally conductive material is a metal in the shape of a bar whose area approximates that of the strip of absorbant material.

5. The assay device of claim 4 wherein the metal is aluminum.

6. The assay device of claim 4 wherein the metal bar is about 1.2 mm thick.

7. The assay device of claim 1 wherein the absorbant strip is made of a bibulous material.

8. The assay device of claim 1 wherein the strip has a fluid test sample application zone which is free of reagent and a reagent containing region which is downstream from and in fluid communication with the reagent containing region.

9. The assay device of claim 3 wherein the plastic is high impact polystyrene, ABS or styrene.

10. A method of determining an analyte in a fluid test sample which comprises applying the fluid test sample to the first region of the strip of claim 1 and observing a detectable response in the detection region of the strip through the pathway.

* * * * *